| United States Patent [19] | [11] Patent Number: 4,996,984 |
| Sweeney | [45] Date of Patent: Mar. 5, 1991 |

[54] DEFIBRILLATION METHOD

[75] Inventor: Robert J. Sweeney, Indianapolis, Ind.

[73] Assignee: Eli Lilly and Company, Indianapolis, Ind.

[21] Appl. No.: 412,753

[22] Filed: Sep. 26, 1989

[51] Int. Cl.$^5$ ............................................. A61N 1/39
[52] U.S. Cl. ............................................. 128/419 D
[58] Field of Search ............................. 128/419 D

[56] References Cited

U.S. PATENT DOCUMENTS 4,559,946 12/1985 Mower ........................... 128/419 D

OTHER PUBLICATIONS

"Cardiovascular Devices and Their Applications", Geddes, John Wiley & Sons, 1984, pp. 302, 310–312.

*Primary Examiner*—William E. Kamm
*Assistant Examiner*—Scott M. Getzow
*Attorney, Agent, or Firm*—Douglas J. Taylor; Leroy Whitaker

[57] ABSTRACT

The present invention provides a method for defibrillating a mammal in need of defibrillation employing multiple bursts of electrical current delivered to the mammal, the timing between said bursts being based upon the mammal's fibrillation cycle length.

27 Claims, No Drawings

DEFIBRILLATION METHOD

BACKGROUND OF THE INVENTION

Ventricular fibrillation is an uncoordinated contraction and relaxation of the individual fibers of the heart which produces no blood flow and results in death unless corrective measures are applied within minutes of onset. Recovery from ventricular fibrillation can be accomplished using drugs or electric shocks. The latter is preferred, mainly because administration of drugs will be of little use in the absence of circulation.

The use of electric shocks to terminate ventricular fibrillation entails passing electric current through the myocardium so as to restore the heart to its natural sinus rhythm. One commonly used method of electric shock therapy involves passing a single burst of electric current through the heart of a patient requiring defibrillation. This single burst may be applied to the heart either transthoracicly from electrodes placed outside the body, or internally from electrodes inside the body normally positioned on, in, or near the heart. Furthermore, the burst of electric current may consist of a monophasic waveform or a multiphasic waveform, for example a biphasic or triphasic waveform. Also, the burst may be applied to one or multiple pathways through the heart depending upon the number of electrodes used and which pulses within the burst are applied across individual electrode pairs. Although efficient in treating the dysrhythmia, the "single burst" method of therapy requires delivering to the patient's heart an electrical pulse of sufficiently high voltage, current and energy that undesirable side effects, such as heart tissue damage and patient discomfort, may result.

To minimize these undesirable side effects, a second method of electric shock therapy utilizes "multiple bursts" of electric current, separated by a fixed time interval. These multiple bursts have consisted of single pulses of electric current separated by a fixed time interval on the order of from 70 to 130 milliseconds. Such "multiple burst" therapy differs from the "single burst" therapy discussed above, in that less voltage, current and energy need be delivered to the patient's heart at any one point in time in order to achieve defibrillation. Accordingly, ventricular defibrillation may be obtained with less patient discomfort and heart tissue damage.

Fibrillation results when many depolarization wavefronts (the locations in the heart where the cell tissue is undergoing depolarization) are moving through the heart in a complicated arrhythmia. When the heart is fibrillating, these depolarization wavefronts pass over any particular portion of the myocardium with a very consistent average timing. The average time interval between successive depolarizations at a particular site in the myocardium is called the fibrillation cycle length.

Prior "multiple burst" defibrillation methods required that the time interval between bursts be some arbitrarily chosen interval. Such methods fail to realize that defibrillation using multiple bursts is optimized when the time interval between bursts is determined by the fibrillation cycle length, rather than by some arbitrary set time interval. Adjusting the time interval between bursts according to the fibrillation cycle length is important since the fibrillation cycle length can vary from mammalian species to mammalian species, from individual to individual within a species, from fibrillation event to fibrillation event in the same individual, and from time to time within the same event.

An object of the present invention is to provide a method of defibrillating the heart of a mammal in need of defibrillation which uses multiple bursts of electrical current delivered to the mammal's heart in a timed relationship to each other which is based upon the mammal's fibrillation cycle length. The instant defibrillation method allows for defibrillation at lower peak voltages and currents, thereby providing defibrillation with a minimum of patient discomfort and heart tissue damage. The instant method's decrease in peak voltages and currents required to accomplish defibrillation also allows improved defibrillator hardware designs and longer defibrillator implant lifetimes.

SUMMARY OF THE INVENTION

The present invention provides a method of defibrillating a mammal in need of defibrillation comprising determining the mammal's fibrillation cycle length; and administering to said mammal a plurality of bursts of electrical current delivered sequentially to said mammal, the timing between said bursts being based upon said mammal's fibrillation cycle length.

DETAILED DESCRIPTION OF THE INVENTION

The present invention provides a method for more effectively defibrillating a mammal's fibrillating heart by first determining the mammal's fibrillation cycle length, and then selecting the number, timing, and/or intensities of a sequence of electrical bursts which are delivered to the mammal in a relationship to each other based upon the measured fibrillation cycle length. A preferred mammalian species which may be defibrillated according to the method of the present invention is the human species.

Normal heart cells have a voltage difference of about 90 millivolts between the outside and the inside of the cell. When the cells are activated this electrical polarization collapses and the cells are said to "depolarize". Heart tissue which is depolarized, and has not had sufficient time to re-establish its voltage difference, is called refractory tissue.

Very shortly after the cells depolarize, they begin to re-establish the voltage difference and are said to "repolarize". It may take several hundred milliseconds for the cells to finish the repolarization process. Tissue which has had enough time to re-establish a sufficiently large voltage polarization, i.e., tissue which is once again susceptible to depolarization, is called non-refractory tissue. The time interval which is required after a cell has been depolarized until it is non-refractory is called the refractory period.

As a cell's voltage polarization collapses, it is capable of activating nearby cells. These nearby cells then, in turn, lose their voltage polarization and stimulate still other cells. In this fashion, depolarization activity can propagate throughout the heart.

At any instant in time, the locations where tissue is depolarizing are called depolarization wavefronts. As depolarization wavefronts move through the heart they leave trails of refractory tissue behind them. This refractory tissue eventually becomes nonrefractory after sufficient time passes.

If the depolarization wavefront reaches tissue which has become non-refractory, it can depolarize that tissue again. When this happens, the depolariztion wavefront may again move throughout the heart over the same pathway. This behavior is called re-entry and the pathway is called a re-entrant pathway.

In a fibrillating heart, depolarization wavefronts move through the myocardium along re-entrant pathways in a complicated arrhythmia. Even though the propagation of wavefronts through the myocardium is complex, individual tissue sections in the myocardium are activated with a surprisingly consistent timing. This timing represents the time required for a depolarization wavefront to traverse a circuit along some re-entrant pathway. The average time required for the wavefront to complete a re-entrant circuit is called the fibrillation cycle length. Many depolarization wavefronts may exist in a fibrillating heart, each moving along its own re-entrant pathway. However, the fibrillation cycle length is also surprisingly consistent between different tissue locations.

Because of the re-entrant nature of fibrillation, at any single instant in time during fibrillation, there will be tissue at all possible timings in the cycle between activations. Along a single re-entrant pathway, the timing of the tissue in its cycle is determined by the motion of the deplorization wavefront along the pathway, with tissue just behind the wavefront being at the beginning of its cycle and tissue just ahead of the wavefront being at the end of its cycle. Since a defibrillation shock is experienced by all tissue at the same time, different tissues along the re-entrant pathway experience the chock at different relative timing in their electrical cycle.

It has been discovered that the effect of the shock on myocardial tissue is to increase the tissue's refractory period. Moreover, the increase depends on the intensity of the shock and also on the relative timing of the shock within the tissue's cycle. Consequently, the influence of a defibrillation shock will be different on different tissues along a re-entrant pathway.

If no shock is delivered, the tissue will repolarize in order around the re-entrant pathway in the same way the previous depolarization wavefront moved. However, the influence of a defibrillation shock may selectively delay the time required for the tissue along the re-entrant pathway to repolarize. Since depolarization wavefronts require repolarized tissue to propagate, a successful defibrillation shock may be used to terminate the depolarization wavefronts by this mechanism.

A subthreshold shock, i.e., an electrical stimulus which is insufficient to terminate depolarization wave propagation by itself, may still be used to alter the timing of the depolarization wavefront along its re-entrant pathways even if the wavefront is not terminated. This is because the depolarization wavefront, even though not terminated by the shock, is still constrained by the subthreshold shock's effect on the timing of tissue repolarization along the re-entrant pathway into which the wavefront must propagate. Accordingly, later subsequent shocks, provided they are delivered in a carefully timed manner, will produce a different pattern of response than the first shock since the tissue has a different repolarization timing pattern than when the first shock was administered. Thus, the effects of a subsequent subthreshold shock or shocks, when combined with the effect produced by the initial subthreshold shock, can be used to terminate propagation of a depolarization wavefront even though neither shock, by itself, is sufficient to terminate propagation.

As noted above, for a series of subthreshold shocks to effect termination of a depolarization wavefront, the shocks must be delivered in a carefully timed manner. If the time duration between successive shocks is too short, the depolarization wavefront which continued after the first shock does not have enough time to return to the re-entrant pathway tissue whose repolarization timing was altered by the first shock. On the other hand, if the time duration between successive shocks is too long, then the depolarization wavefront which continued after the first shock has sufficient time to sweep past the portion of the re-entrant pathway whose repolarization timing was altered by the first shock. In either case, the ability of the preceeding shock to enhance the influence of subsequent shocks is reduced.

The present invention uses a series of subthreshold shocks to defibrillate a mammal in need of defibrillation. To ensure the subsequent subthreshold shock or shocks are delivered at the most optimal (in terms of depolarization wavefront termination) time, the present invention requires that the patient's fibrillation cycle length be determined before the first shock is administered. Once the patient's fibrillation cycle length has been established, the timing between successive shocks is determined in terms of a certain percentage of the fibrillation cycle length. In this fashion, a second shock can be delivered after a depolarization wavefront has completed a known percentage of its re-entrant pathway relative to its position when the first shock was delivered. A third shock may then be timed relative to the second shock, and so on. Basing the delivery time of a plurality of shocks upon the fibrillation cycle length ensures the shocks are delivered in a more optimal defibrillatory manner than can be obtained if the electrical bursts are administered based upon some arbitrarily chosen fixed time interval between bursts.

The initial step of the present method of defibrillating a mammal in need of defibrillation requires that the patient's fibrillation cycle length be determined. The fibrillation cycle length of a fibrillating heart can be obtained using methods well known to those skilled in the art, including a number of signal processing methods such as cross-correlation, auto-correlation, fast Fourier transformation, counting the R waves of the electrocardiogram over a fixed time period and determining the R-R intervals of individual electrocardiograms. The use of auto-correlation to determine the fibrillation cycle length is illustrated in references such as Angelakos et al., *Cir. Res.*, 5, 657 (1957) and Chen et al., *Med. and Biol. Eng. and Computing*, 25, 241 (1987). The following references illustrate the use of fast Fourier transformation to determine the fibrillation cycle length; Carlisle, *Br. Heart J.*, 59, 85 (1988) and Strootbandt et al., *Pace*, 8, 502 (1985). Finally, Black et al., *J. A. C. C.*, 9(2), 142A (1987); Farges et al., *Br. J. Pharmac.*, 63, 587 (1987); and Worley et at. *Am. J. Cardiol.*, 55, 813 (1985) use a counting technique over a fixed time period or measure R-R intervals to determine the fibrillation cycle length. The teachings of these references is herein incorporated by reference.

In some patients the fibrillation cycle length may be relatively constant from fibrillation event to fibrillation event. For these individuals the present method requires that the fibrillation cycle length need only be determined once, since, in any subsequent fibrillation event, the fibrillation cycle length will be approximately equivalent to that originally measured. In other patients, however, the fibrillation cycle length will vary from fibrillation event to fibrillation event. For these patients, the present method requires that the fibrillation cycle length be determined for each fibrillation event.

Once a patient's fibrillation cycle length has been determined, defibrillation can be accomplished by administering a plurality of bursts of electrical current, i.e., shocks, sequentially to the patient. The shocks are administered using methods well known to those skilled in the art of electrical impulse defibrillation. Internal or external methods for administering electrical bursts may be used to administer the plurality of electrical bursts required by the present invention. Internal methods of administration, i.e., delivering shocks to the heart of a patient, are preferred.

Moreover, if more than two electrodes are used to deliver the chock, the chock may be delivered through multiple, different, pathways. Normally, the multiple pathways are shocked at essentially the same time, with usually about a 0.2 Millisecond period between shocks. However, in certain cases, each pathway might be shocked at different times. All of the above are methods of administering shocks which are well known to those skilled in the art and are, therefore, encompassed within the present method.

The timing between shocks, which is a crucial feature of the present invention, is based upon the patient's fibrillation cycle length. In general, each succeeding shock will be delivered at a chosen time interval, set to be in the range of from about 30% to about 200% of the patient's fibrillation cycle length, after the preceeding shock has been administered. A preferred time interval range for administering successive shocks is from about 60% to about 85% of the fibrillation cycle length. Successive shocks are most preferably administered at a time interval which is about 75% of the patient's fibrillation cycle length.

The number of subthreshold shocks required to defibrillate is not crucial. While defibrillation using two shocks is preferred, defibrillation using three, four, five or even more shocks is also encompassed within the scope of the present invention provided the timing between successive shocks is based upon the previously determined fibrillation cycle length. If more than two chocks are administered, the time interval between the second and third shocks, the third and fourth shocks, etc., need not be the same time interval as that used between previously administered shocks.

The current, voltage, type and duration of electrial bursts employed can vary widely so long as the resultant shock is a subthreshold shock. The bursts may consist of monophasic or multiphasic, including biphasic or triphasic, waveforms. Furthermore, the electrical bursts used to produce the successive subthreshold shocks required by the present invention need not be identical, i.e., the first electrical burst may differ from the second burst, which may differ from the third, etc. Typical current, voltage and electrical burst duration ranges, as well as types of electrical bursts which may be employed, are as described below.

The voltage range described below is suitable for internal administration of electrical bursts. External administration of electrical bursts requires, as is well known to those skilled in the art, significantly higher voltage levels than those set forth below. Suitable voltage ranges for external electrical impulse defibrillation are well known to the artisan and therefore will not be described below.

The current supplied by the electrical burst may vary from about 0.4 amps to about 16 amps. A preferred current range is from about 4 amps to about 10 amps.

The voltage delivered by the electrical burst will vary from about 20 to about 800 volts. A more preferred voltage range is from about 100 to about 500 volts. The electrical burst will most preferably deliver from about 200 to about 300 volts.

The duration of electrical burst used to provide a subthreshold shock may vary from about 1 millisecond to about 40 milliseconds, more preferably from about 5 milliseconds to about 25 milliseconds. A most preferred electrical burst duration will be from about 8 milliseconds to about 15 milliseconds.

The type of electrical burst used in the present invention may be any type of electrical burst waveform commonly known in the art. Examples of such waveforms include standard truncated exponential waveforms such as those described by Schuder et al., *Trans. Am. Soc. Artif. Organs*, 15, 207 (1970); rectangular pulse waveforms; trapezoidal shaped waveforms; square pulse waveforms; and the like. A standard truncated exponential waveform is preferred for use in the present invention.

To illustrate the presently claimed method of defibrillation, and its advantages relative to other defibrillation techniques, the following experiments were conducted. The experiments are not intended to limit the scope of the invention in any respect and should not be so construed.

Multiple Bursts—Fixed Time Interval vs. Time Interval Based on a Percentage of Fibrillation Cycle Length Open-chested, pentobarbital-anesthetized dogs were implanted with a spring-patch configuration of defibrillation electrodes and with twelve plunge recording electrodes in the left and right side of the myocardium. The animals were electrically induced into fibrillation. A computer was used to sample the electrograms from the recording electrodes during the first 15 seconds of the fibrillation event and to determine the fibrillation cycle length by finding the average R-R interval of individual electrocardiograms.

The computer then triggered the defibrillation attempt by activating two defibrillators such that the timing between the delivered shocks was a pre-determined percentage of the fibrillation cycle length. Each defibrillator produced a monophasic, truncated exponential shock with a 63% tilt and with identical leading edge voltages. The animals were than observed to see if the shocks were able to convert the ventricular fibrillation to a normal sinus rhythm.

If normal sinus rhythm was restored another fibrillation was initiated after a three minute delay. If normal sinus rhythm was not restored, then the animal was immediately rescued with a shock of 15 to 20 joules and another fibrillation was initiated after a three minute delay. Depending on the outcome of the previous defibrillation attempt, the energy of the defibrillation shocks was adjusted upwards or downwards according to a fixed protocol which yielded the 50 percent success defibrillation threshold (i.e. the energy (per shock) which would be expected to defibrillate 50 percent of the time). The above process was then repeated at four different pre-determined percentages of the fibrillation cycle length.

The same experimental sequence was then repeated after administering clofilium to the test animals.

Clofilium slows down fibrillation, thus increasing fibrillation cycle length. The defibrillation threshold energies of non-clofillium treated animals were compared to those of clofilium treated animals to determine if defibrillation threshold energy corresponds to absolute time separation (DT) between shocks, or to a time interval based on a percentage of the fibrillation cycle length. The results are set forth in Tables I and II below.

Table I provides the test results obtained from one test animal Column 6 of Table I provides the percentage of the fibrillation cycle length (FCL) at which the second electrical shock was delivered. Columns 5 and 7 provide the measured fibrillation cycle lengths, in milliseconds, of the non-clofilium and clofilium treated experiments, respectively. Columns 4 and 8 disclose the absolute time separation (DT) between shocks in the non-clofilium and clofilium treated experiments, respectively. Columns 3 and 9 disclose the respective defibrillation thresholds (DFT) energies, obtained as described above. Finally, Columns 1, 2, 10 and 11 provide the electrical voltages and currents corresponding to the DFT energies of Columns 3 and 9.

Table II provides the test results obtained using a second test animal. The table's format is the same as that described for Table I.

ensures optimal timing between defibrillation shocks, the claimed method provides defibrillation at a lower maximum energy input. Accordingly, the present method provides defibrillation with less heat tissue damage and patient discomfort.

Secondly, since the present method provides defibrillation at low energy inputs, the energy which must be supplied by the defibrillator is less than that which would be required if conventional (fixed time interval) "multiple burst" defibrillation methods were employed. The less energy which must be supplied by the defibrillator, the smaller the defibrillator battery size required. This, in turn, allows for defibrillator hardware designs which are more aesthetic, and more practical, due to the smaller equipment size required.

Finally, if one chooses to keep the same defibrillator battery size, the lower energy inputs required by the present method provides for longer battery life. Such advantage is especially important in the case of implantable defibrillators, where replacement of a discharged battery requires surgery.

Single Burst Defibrillation vs. Multiple Burst Defibrillation Using a Time Interval Based on a Percentage of the Fibrillation Cycle Length

TABLE I

| Absolute Time Interval vs. Time Interval Based on Percentage of FCL | | | | | | | | | | |
|---|---|---|---|---|---|---|---|---|---|---|
| Non-clofilium Treated | | | | | | Clofilium Treated | | | | |
| Estimated Current (Amp)* | Voltage (Volts) | DFT Energy (Joules) | DT (msec) | FCL (msec) | % FCL | FCL (msec) | DT (msec) | DFT Energy (Joules) | Voltage (Volts) | Estimated Current (Amp)* |
| 6.2 | 311 | 5.7 | 50.4 | 91.7 | 55 | 108.2 | 59.7 | 7.0 | 346 | 6.9 |
| 5.6 | 280 | 4.7 | 59.3 | 91.5 | 65 | 103.4 | 67.4 | 4.3 | 268 | 5.4 |
| 4.1 | 203 | 2.7 | 72.5 | 95.8 | 75 | 114.2 | 85.8 | 3.0 | 225 | 4.5 |
| 4.3 | 213 | 3.0 | 79.0 | 92.8 | 85 | 110.7 | 94.0 | 5.3 | 299 | 6.0 |
| 4.5 | 226 | 3.0 | 87.3 | 92.6 | 95 | 113.0 | 107.7 | 4.7 | 281 | 5.6 |

TABLE II

| Absolute Time Interval vs. Time Interval Based on Percentage of FCL | | | | | | | | | | |
|---|---|---|---|---|---|---|---|---|---|---|
| Non-clofilium Treated | | | | | | Clofilium Treated | | | | |
| Estimated Current (Amp)* | Voltage (Volts) | DFT Energy (Joules) | DT (msec) | FCL (msec) | % FCL | FCL (msec) | DT (msec) | DFT Energy (Joules) | Voltage (Volts) | Estimated Current (Amp)* |
| 7.9 | 397 | 9.0 | 48.8 | 88.7 | 55 | 102.3 | 56.6 | 8.0 | 374 | 7.5 |
| 7.4 | 372 | 8.0 | 56.4 | 86.8 | 65 | 100.2 | 65.2 | 7.0 | 351 | 7.0 |
| 6.1 | 306 | 5.3 | 65.9 | 87.7 | 75 | 103.2 | 77.8 | 6.0 | 325 | 6.5 |
| 7.0 | 351 | 7.0 | 74.6 | 87.6 | 85 | 101.3 | 86.1 | 6.3 | 337 | 6.7 |
| 7.3 | 365 | 7.7 | 83.0 | 87.2 | 95 | 96.3 | 91.3 | 7.7 | 360 | 7.2 |

*Based on the assumption the heart has an impedance of approximately 50 Ohms.

As can be seen from TAbles I and II, above, the minimum energy required to defibrillate was obtained, in both the non-clofilium and clofilium experiments, when the electrical bursts were administered at a time interval which was 75% of the fibrillation cycle length. In the non-clofilium experiments, 75% of the cycle length was 69.2±4.7 milliseconds. Upon treatment with clofilium 75% of the cycle length was now 81.8±5.7 milliseconds. Thus, the fact that the optimal time interval (optimal in terms of ability to defibrillate for the least amount of energy supplied) differs between the two experiments establishes that the optimal interval between multiple shock bursts can best be obtained if the timing between bursts is based on the fibrillation cycle length.

The present defibrillation method provides several advantages over "multiple burst" defibrillation techniques which use an arbitrarily chosen fixed time interval between bursts. First, since the present method Open-chested pentobarbital anesthetized dogs were implanted with defibrillation electrodes and recording electrodes as described above. Fibrillation was induced and a computer was used to determine the fibrillation cycle length from the recording electrodes and to trigger the defibrillation attempt. The effectiveness of single chock defibrillation attempts and two shock defibrillation attempts (each shock had half the total energy of the single shock) were compared by repeating the fibrillation/defibrillation sequence many times and noting the percentage of successful defibrillation attempts. An unsuccessful attempt was always immediately followed with a rescue shock of 15–20 joules. When two defibrillation shocks were employed, the timing between shocks was a pre-determined percentage of the fibrillation cycle length. All shocks were monophasic, truncated exponential waveforms with a 63% tilt and with identical leading edge voltages.

The results of the above experiment are provided in Tables III and IV, below. Table III discloses the results obtained using a single defibrillation shock. In Table III, Column 1 provides the total shock energy delivered to the test animals. Column 2, 3 and 4 disclose the energy, voltage and current, respectively, of the electrical burst administered. Finally, Column 5 discloses the number of successful defibrillation attempts/number of defibrillations attempted.

Table IV discloses the results obtained using multiple defibrillation shocks. In Table IV, Column 1 provides the total shock energy delivered to the test animals. Columns 2, 3 and 4 disclose the energy, voltage and current, respectively, of each electrical pulse administered. Finally, Column 5, 6 and 7 disclose the number of successful defibrillation attempts/number of defibrillations attempted when multiple shocks were administered at time intervals corresponding to 33%, 75% and 100%, respectively, of the fibrillation cycle length.

TABLE III

| | Single Defibrillation Burst | | | |
|---|---|---|---|---|
| Total Shock Energy (Joules) | Shock Energy/Shock (Joules) | Voltage/Shock (Volts) | EStimated Current/Shock (Amps)* | # defibrillations/# attempted |
| 8 | 8 | 370 | 7.4 | 16/20 |
| 6 | 6 | 326 | 6.5 | 7/10 |

TABLE IV

| | Multiple Defibrillation Bursts | | | | | |
|---|---|---|---|---|---|---|
| Total Shock Energy (Joules) | Shock Energy/Shock (Joules) | Voltage/Shock (Volts) | Estimated Current/Shock (Amps)* | # defibrillation/# attempted | | |
| | | | | 33% FCL | 75% FCL | 100% FCL |
| 8 | 4 | 260 | 5.2 | 3/10 | 12/20 | 9/20 |
| 6 | 3 | 220 | 4.4 | 0/5 | 7/10 | 5/10 |

*Based on the assumption the heart has an impedance of approximately 50 Ohms.

As can be seen from Tables III and IV, above, the multiple burst defibrillation method of the present invention can be used to defibrillate a patient in need of defibrillation. In fact, if the shocks are administered at a time interval corresponding to approximately 75% of the patient's fibrillation cycle length, the present defibrillation method has a defibrillation success rate comparable to that which can be achieved using "single burst" defibrillation techniques. Accordingly, the present method provides important advantages over conventional "single burst" defibrillation methods, in terms of minimizing patient discomfort and heart tissue damage, since less voltage, current and energy must be supplied to the patient at any one point in time in order to accomplish defibrillation.

I claim:

1. A method of defibrillating a mammal in need of defibrillation comprising:
   (a) first determining the mammal's fibrillation cycle length; and
   (b) then administering to said mammal a plurality of bursts of electrical current delivered sequentially to said mammal, adjusting the timing between said bursts based upon said mammal's fibrillation cycle length.

2. A method of claim 1 wherein the plurality of bursts consists of two bursts.

3. A method of claim 2 wherein the timing between the two bursts of electrical current is from about 30% to about 200% of the mammal's fibrillation cycle length.

4. A method of claim 3 wherein the timing between bursts is from about 60% to about 85% of the mammal's fibrillation cycle length.

5. A method of claim 4 wherein the timing between bursts is about 75% of the mammal's fibrillation cycle length.

6. A method of claim 1 wherein the plurality of bursts consists of three bursts.

7. A method of claim 1 wherein the timing between each pair of bursts of electrical current is independently from about 30% to about 200% of the mammal's fibrillation cycle length.

8. A method of claim 7 wherein the timing between each pair of bursts is independently from about 60% to about 85% of the mammal's fibrillation cycle length.

9. A method of claim 8 wherein the timing between each pair of bursts is independently about 75% of the mammal's fibrillation cycle length.

10. A method of claim 1 wherein the bursts of electrical current are administered within the body of the mammal.

11. A method of claim 10 wherein the plurality of bursts consists of two bursts.

12. A method of claim 10 wherein the voltage of each burst is from about 20 volts to about 800 volts.

13. A method of claim 12 wherein the voltage is from about 100 volts to about 500 volts.

14. A method of claim 13 wherein the voltage is from about 200 volts to about 300 volts.

15. A method of claim 10 wherein the timing between each pair of bursts of electrical current is independently from about 30% to about 200% of the mammal's fibrillation cycle length.

16. A method of claim 15 wherein the timing between each pair of bursts is independently from about 60% to about85% of the mammal's fibrillation cycle length.

17. A method of claim 16 wherein the timing between each pair of bursts is independently about 75% of the mammal's fibrillation cycle length.

18. A method of claim 16 wherein the plurality of bursts consists of two bursts; the current of each burst is from about 4 amps to about 10 amps; the voltage of each burst is from about 200 volts to about 300 volts; and the duration of each burst is from about 8 milliseconds to about 15 milliseconds.

19. A method of claim 18 wherein each burst is a standard truncated exponential waveform burst.

20. A method of claim 1 wherein the current of each burst is from about 0.4 amps to about 16 amps.

21. A method of claim 20 wherein the current is from about 4 amps to about 10 amps.

22. A method of claim 1 wherein the duration of each burst is from about 1 millisecond to about 40 milliseconds.

23. A method of claim 22 wherein the duration of each burst is from about 5 milliseconds to about 25 milliseconds.

24. A method of claim 23 wherein the duration of each burst is from about 8 milliseconds to about 15 milliseconds.

25. A method of claim 1 wherein each burst is a standard truncated exponential waveform burst.

26. A method of defibrillating a mammal in need of defibrillation comprising:
 (a) first determining the mammal's fibrillation cycle length; and
 (b) then administering to said mammal two bursts of electrical current delivered sequentially to said mammal; the current of each burst being from about 4 amps to about 10 amps; the voltage of each burst being from about 200 volts to about 300 volts; the duration of each burst being from about 8 milliseconds to about 15 milliseconds; and adjusting the timing between bursts to about 75% of the mammal's fibrillation cycle length.

27. A method of claim 26 wherein each burst is a standard truncated exponential waveform burst.

* * * * *